(12) United States Patent
Aylsworth et al.

(10) Patent No.: US 10,953,172 B2
(45) Date of Patent: Mar. 23, 2021

(54) METHOD AND SYSTEM OF SENSING AIRFLOW AND DELIVERING THERAPEUTIC GAS TO A PATIENT

(71) Applicant: INCOBA, LLC, Wildwood, MO (US)

(72) Inventors: Alonzo C. Aylsworth, Wildwood, MO (US); Lawrence C. Spector, Driftwood, TX (US)

(73) Assignee: Incoba, LLC, Wildwood, MO (US)

( * ) Notice: Subject to any disclaimer, the term of this patent is extended or adjusted under 35 U.S.C. 154(b) by 977 days.

(21) Appl. No.: 15/478,388

(22) Filed: Apr. 4, 2017

(65) Prior Publication Data

US 2017/0203062 A1 Jul. 20, 2017

Related U.S. Application Data

(63) Continuation of application No. PCT/US2015/054391, filed on Oct. 7, 2015.
(Continued)

(51) Int. Cl.
*A61M 16/00* (2006.01)
*A61M 16/10* (2006.01)
(Continued)

(52) U.S. Cl.
CPC ...... *A61M 16/0003* (2014.02); *A61M 16/024* (2017.08); *A61M 16/0666* (2013.01); *A61M 16/0677* (2014.02); *A61M 16/0816* (2013.01); *A61M 16/10* (2013.01); *A61M 16/202* (2014.02); *A61M 16/0672* (2014.02); *A61M 2016/003* (2013.01);
(Continued)

(58) Field of Classification Search
CPC ............ A61M 16/0003; A61M 16/024; A61M 16/0666; A61M 16/0672; A61M 16/0677; A61M 16/10; A61M 16/202; A61M 2016/0015; A61M 2016/0027; A61M 2016/003; A61M 2016/0039
See application file for complete search history.

(56) References Cited

U.S. PATENT DOCUMENTS 5,060,514 A 10/1991 Aylsworth
5,313,820 A 5/1994 Aylsworth
(Continued)

FOREIGN PATENT DOCUMENTS

WO 2014/089223 A1 6/2014

OTHER PUBLICATIONS

European Patent Office, Office Action in related EP application No. 15849641.4-1122, dated Apr. 14, 2020; 6 pages.
(Continued)

*Primary Examiner* — Kathryn E Ditmer
(74) *Attorney, Agent, or Firm* — Mark E. Scott; Dickinson Wright PLLC

(57) ABSTRACT

Sensing airflow and delivering therapeutic gas to a patient. At least some of the example embodiments are methods including: titrating a patient with therapeutic gas during a period of time when a flow state of breathing orifices is in a first state, the titrating results in a prescription titration volume; and then delivering the prescription titration volume of therapeutic gas to the patient when the flow state of the breathing orifices is in a second state different than the first state, the delivering only to the breathing orifices open to flow.

12 Claims, 9 Drawing Sheets

Related U.S. Application Data

(60) Provisional application No. 62/060,617, filed on Oct. 7, 2014.

(51) Int. Cl.
*A61M 16/06* (2006.01)
*A61M 16/20* (2006.01)
*A61M 16/08* (2006.01)

(52) U.S. Cl.
CPC .............. *A61M 2016/0015* (2013.01); *A61M 2016/0027* (2013.01); *A61M 2016/0039* (2013.01); *A61M 2202/0208* (2013.01); *A61M 2210/0618* (2013.01); *A61M 2230/005* (2013.01); *A61M 2230/205* (2013.01); *A61M 2230/40* (2013.01)

(56) References Cited

U.S. PATENT DOCUMENTS

| | | |
|---|---|---|
| 5,369,979 A | 12/1994 | Aylsworth et al. |
| 5,495,848 A | 3/1996 | Aylsworth et al. |
| 5,746,806 A | 5/1998 | Aylsworth et al. |
| 5,890,490 A | 4/1999 | Aylsworth et al. |
| 6,904,913 B2 | 6/2005 | Aylsworth et al. |
| 7,007,692 B2 * | 3/2006 | Aylsworth ........ A61M 16/0666 128/203.22 |
| 7,007,694 B2 | 3/2006 | Aylsworth et al. |
| 7,013,898 B2 * | 3/2006 | Rashad ............. A61M 16/0666 128/207.18 |
| 7,066,180 B2 | 6/2006 | Aylsworth et al. |
| 7,114,497 B2 | 10/2006 | Aylsworth et al. |
| 7,150,280 B2 | 12/2006 | Aylsworth et al. |
| 7,153,271 B2 | 12/2006 | Aylsworth |
| D538,927 S | 3/2007 | Aylsworth et al. |
| D540,463 S | 4/2007 | Aylsworth et al. |
| 7,213,594 B2 | 5/2007 | Aylsworth et al. |
| 7,267,123 B2 | 9/2007 | Aylsworth et al. |
| 8,776,793 B2 | 7/2014 | Wondka et al. |
| 9,056,179 B2 | 6/2015 | Aylsworth et al. |
| 2003/0140924 A1 | 7/2003 | Aylsworth et al. |
| 2004/0079359 A1 | 4/2004 | Aylsworth et al. |
| 2005/0005942 A1 | 1/2005 | Aylsworth et al. |
| 2005/0011523 A1 | 1/2005 | Aylsworth et al. |
| 2005/0092321 A1 | 5/2005 | Aylsworth et al. |
| 2005/0145248 A1 | 7/2005 | Aylsworth et al. |
| 2005/0257788 A1 | 11/2005 | Aylsworth et al. |
| 2005/0257794 A1 | 11/2005 | Aylsworth et al. |
| 2005/0261600 A1 | 11/2005 | Aylsworth |
| 2005/0268912 A1 | 12/2005 | Norman et al. |
| 2006/0005834 A1 | 1/2006 | Aylsworth et al. |
| 2006/0005842 A1 | 1/2006 | Rashad et al. |
| 2006/0090759 A1 * | 5/2006 | Howes ............... A61M 16/101 128/204.21 |
| 2006/0169281 A1 * | 8/2006 | Aylsworth ........ A61M 16/0666 128/204.23 |
| 2006/0174883 A1 | 8/2006 | Aylsworth et al. |
| 2006/0174885 A1 | 8/2006 | Aylsworth et al. |
| 2006/0254588 A1 | 11/2006 | Brewer et al. |
| 2006/0272643 A1 | 12/2006 | Aylsworth et al. |
| 2007/0186929 A1 | 8/2007 | Aylsworth et al. |
| 2007/0272239 A1 | 11/2007 | Aylsworth et al. |
| 2007/0272240 A1 | 11/2007 | Aylsworth et al. |
| 2007/0277824 A1 | 12/2007 | Aylsworth et al. |
| 2008/0006271 A1 | 1/2008 | Aylsworth et al. |
| 2008/0142011 A1 | 6/2008 | Aylsworth et al. |
| 2008/0257145 A1 | 10/2008 | Sprinkle et al. |
| 2010/0186741 A1 | 7/2010 | Aylsworth et al. |
| 2012/0053481 A1 | 3/2012 | Aylsworth |
| 2012/0065533 A1 | 3/2012 | Carrillo, Jr. et al. |
| 2013/0012828 A1 | 1/2013 | Aylsworth |
| 2013/0131534 A1 | 5/2013 | Heatherington et al. |
| 2014/0150789 A1 * | 6/2014 | Flanagan .......... A61M 16/0677 128/203.22 |

OTHER PUBLICATIONS

Search Report dated Jun. 18, 2018 in European Patent Application No. 15849641.4 filed Jul. 28, 2017; 10 pages.

International Search Report and Written Opinion dated Jan. 18, 2016; Application No. PCT/US2015/054391 filed Oct. 7, 2015; 11 pages.

\* cited by examiner

METHOD AND SYSTEM OF SENSING AIRFLOW AND DELIVERING THERAPEUTIC GAS TO A PATIENT

CROSS-REFERENCE TO RELATED APPLICATIONS

This application is a continuation of International Application No. PCT/US2015/054391 filed Oct. 7, 2015 and titled "Method and System of Sensing Airflow and Delivering Therapeutic Gas to a Patient", which claims the benefit of U.S. Provisional Application No. 62/060,617 filed Oct. 7, 2014 and titled "Selective Delivery of Therapeutic Gas". Both applications are incorporated by reference herein as if reproduced in full below.

BACKGROUND

Patients with respiratory ailments may be required to breathe therapeutic gas, such as oxygen. The therapeutic gas may be delivered to the patient from a therapeutic gas source by way of a nasal cannula.

Delivery of therapeutic gas to a patient may be continuous, or in a conserve mode. In continuous delivery, the therapeutic gas may be supplied at a constant flow rate throughout the patient's breathing cycle. A significant portion of the therapeutic gas provided in continuous delivery is wasted (i.e., the therapeutic gas delivered during exhalation of the patient is lost to atmosphere). In order to overcome the wastefulness of continuous delivery, related-art devices may operate in conserve mode using a conserver system.

A conserver system may be a device which senses a patient's inspiration, and delivers a bolus of therapeutic gas only during inspiration. By delivering therapeutic gas only during inspiration, the amount of therapeutic gas lost to atmosphere may be reduced. Conserver systems of the related art may sense a patient's inspiration at one nare and deliver the bolus of therapeutic gas to the other nare, such as through a bifurcated nasal cannula. Alternatively, conserver devices of the related art may sense a patient's inspiration at the nares generally, and delivery a bolus of therapeutic gas to the nares generally, such as through a non-bifurcated (single lumen) nasal cannula.

Sensing at one naris and delivering to a second naris may not work properly in all situations. If the patient has a blocked nare (e.g., because of congestion or some physical abnormality), either the sensing may not operate properly or the delivery of therapeutic gas may be to the blocked nare. Sensing and/or delivery may also fail to operate properly if the nasal cannula becomes dislodged, such as during sleep.

When sensing inspiration by monitoring both nares simultaneously, congestion and/or abnormalities in the nares may cause the system to not sense properly. Moreover, when delivering therapeutic gas to the nares generally, such as through a single lumen cannula, congestion and/or physical abnormalities of the nares may affect the volume inhaled in each naris, wasting therapeutic gas in some cases and not providing sufficient therapeutic gas in other cases.

SUMMARY

According to a first aspect there is provided a method comprising: receiving a prescription titration volume, the prescription titration volume being generated by titrating a patient with therapeutic gas during a period of time when a flow state of breathing orifices is in a first state; receiving an indication that a flow state of the breathing orifices is in a second state different than the first state; and outputting a control signal arranged to cause the prescription titration volume of therapeutic gas to be delivered to the patient only to the breathing orifices open to flow.

Receiving a prescription titration volume may comprise: receiving individually sensed airflow of a plurality of the breathing orifices of the patient; determining whether the breathing orifices are open to flow, the determining based on the individually sensed airflow of a plurality of the breathing orifices; outputting a control signal arranged to cause a bolus of therapeutic gas to be provided to each breathing orifice that is open to flow, the providing during each of a plurality of inhalations of the patient, each bolus has a volume; receiving a measured oxygen saturation of the patient; determining an adjusted set point volume of the bolus; repeating the receiving individually sensed airflow, outputting, receiving a measured oxygen saturation and determining steps until the patient's oxygen saturation resides within a predetermined range; and calculating the prescription titration volume as a sum of the volumes of each bolus provided during an inhalation when patient's oxygen saturation resides within the predetermined range.

Receiving a prescription titration volume may further comprise: receiving individually sensed airflow of each of a first nare and a second nare of the patient; determining whether the first and second nares are open to flow, the determining based on the received individually sensed airflow; outputting a control signal arranged to cause a bolus of therapeutic gas to be provided to each nare that is open to flow, the providing during each of a plurality of inhalations of the patient, each bolus has a volume; receiving a measured oxygen saturation of the patient; determining an adjusted set point volume of the bolus; repeating the receiving individually sensed airflow, outputting, receiving a measured oxygen saturation and determining steps until the patient's oxygen saturation resides within a predetermined range; and calculating the prescription titration volume as a sum of the volumes of each bolus provided during an inhalation when patient's oxygen saturation resides within the predetermined range.

The prescription titration volume may be generated by titrating the patient with therapeutic gas during the first state wherein both nares of the patient are open to flow, the titrating results in the prescription titration volume; and the output control signal may be arranged to cause therapeutic gas to be delivered to the patient by delivering therapeutic gas in the second state wherein only one nare is open to flow, the delivering by providing prescription titration volume only to the nare open to flow.

The prescription titration volume may be generated by titrating the patient with therapeutic gas during the first state wherein only one nare of the patient is open to flow, the titrating results in the prescription titration volume; and the output control signal may be arranged to cause therapeutic gas to be delivered during the second state wherein both nares are open to flow, the delivering by providing a first non-zero portion of the prescription titration volume to a first nare and providing a second portion of the prescription titration volume to a second nare.

The output control signal may be arranged to cause gas to be delivered by, during each inhalation: receiving individually sensed airflow of the breathing orifice of the patient; determining whether the breathing orifices are open to flow, the determining based on the individually sensed airflow;

and outputting a signal arranged to cause the prescription titration volume to be divided among the breathing orifices open to flow.

The output control signal may be arranged to cause gas to be delivered by, during an inhalation: receiving individually sensed airflow of a first breathing orifice and a second breathing orifice of the patient; determining initially that the first breathing orifice is open to flow and the second breathing orifice is closed to flow, the determining based on the individually sensing; outputting a control signal arranged to cause delivery of the therapeutic gas to the first breathing orifice to begin; and then determining that during the inhalation the second breathing orifice opens to flow; and outputting a control signal arranged to cause delivery of the therapeutic gas to begin to the second breathing orifice after beginning delivery of therapeutic gas to the first breathing orifice; and outputting a control signal arranged to cause delivery of therapeutic gas to cease to both orifices when the total volume delivered is the prescription titration volume.

According to a second aspect of the invention there is provided a method comprising: titrating a patient with therapeutic gas during a period of time when a flow state of breathing orifices is in a first state, the titrating results in a prescription titration volume; and then delivering the prescription titration volume of therapeutic gas to the patient when the flow state of the breathing orifices is in a second state different than the first state, the delivering only to the breathing orifices open to flow.

Titrating may further comprise: individually sensing airflow of a plurality of the breathing orifices of the patient; determining whether the breathing orifices are open to flow, the determining based on the individually sensing; providing a bolus of therapeutic gas to each breathing orifice that is open to flow, the providing during each of a plurality of inhalations of the patient, each bolus has a volume; measuring oxygen saturation of the patient; adjusting a set point volume of the bolus; repeating the sensing, providing, measuring and adjusting steps until the patient's oxygen saturation resides within a predetermined range; and calculating the prescription titration volume as a sum of the volumes of each bolus provided during an inhalation when patient's oxygen saturation resides within the predetermined range.

Titrating may further comprise: individually sensing airflow of each of a first nare and a second nare of the patient; determining whether the first and second nares are open to flow, the determining based on the individually sensing; providing a bolus of therapeutic gas to each nare that is open to flow, the providing during each of a plurality of inhalations of the patient, each bolus has a volume; measuring oxygen saturation of the patient; adjusting a set point volume of the bolus; repeating the sensing, providing, measuring and adjusting steps until the patient's oxygen saturation resides within a predetermined range; and calculating the prescription titration volume as a sum of the volumes of each bolus provided during an inhalation when patient's oxygen saturation resides within the predetermined range.

Titrating may further comprise titrating the patient with therapeutic gas during the first state wherein both nares of the patient are open to flow, the titrating results in the prescription titration volume; and wherein delivering therapeutic gas to the patient may further comprise delivering therapeutic gas in the second state wherein only one nare is open to flow, the delivering by providing prescription titration volume only to the nare open to flow.

Titrating the patient with therapeutic gas may further comprise titrating during the first state wherein only one nare of the patient is open to flow, the titrating results in the prescription titration volume; and delivering therapeutic gas to the patient may further comprise delivering therapeutic gas during the second state wherein both nares are open to flow, the delivering by providing a first non-zero portion of the prescription titration volume to a first nare and providing a second portion of the prescription titration volume to a second nare.

Delivering therapeutic gas may further comprise, during each inhalation: individually sensing airflow of the breathing orifice of the patient; determining whether the breathing orifices are open to flow, the determining based on the individually sensing; and delivering the therapeutic gas by dividing the prescription titration volume among the breathing orifices open to flow.

Delivering therapeutic gas may further comprise, during an inhalation: individually sensing airflow of a first breathing orifice and a second breathing orifice of the patient; determining initially that the first breathing orifice is open to flow and the second breathing orifice is closed to flow, the determining based on the individually sensing; beginning delivery of the therapeutic gas to the first breathing orifice; and then determining that during the inhalation the second breathing orifice opens to flow; and beginning delivery of the therapeutic gas to the second breathing orifice after beginning delivery of therapeutic gas to the first breathing orifice; and ceasing delivery of therapeutic gas to both orifices when the total volume delivered is the prescription titration volume.

According to a further aspect there is provided a conserver system comprising: a therapeutic gas port configured to couple to a source of therapeutic gas; a first port configured to fluidly couple to a first breathing orifice of a patient; a second port configured to fluidly couple to a second breathing orifice of the patient; wherein, during a first inhalation of a patient, the conserver system fluidly couples the gas port to the first port when airflow through the first breathing orifice is sensed by the conserver system, and the conserver system refrains from fluidly coupling the gas port to the second port when airflow through the second breathing orifice is not sensed by the conserver system; wherein, during the first inhalation, the conserver system decouples the gas port from the first port when a volume of therapeutic gas delivered to the first port equals a prescription titration volume; wherein, during a second inhalation, the conserver system fluidly couples the gas port to the first port when airflow through the first breathing orifice is sensed, and the conserver system fluidly couples the gas port to the second port when airflow through the second breathing orifice is sensed; and wherein, during the second inhalation, the conserver system decouples the gas port from the first and second ports during the second inhalation when a volume of therapeutic gas delivered to the first and second breathing orifices equals the prescription titration volume.

The order of the inhalations may be at least one selected from the group consisting of: the first inhalation precedes the second inhalation; the second inhalation precedes the first inhalation; the first inhalation immediately precedes the second inhalation; the second inhalation immediately precedes the first inhalation.

The conserver system may further comprise a pressure sensor fluidly coupled to the first port, the pressure sensor configured to sense airflow of the first breathing orifice based on changes in sensed pressure.

The conserver system may comprise a sensor fluidly associated with the second port, the second sensor being at least one selected from the group consisting of: a pressure sensor; and a flow sensor.

The conserver system may further comprise a flow sensor fluidly coupled within the flow path of the first port, the flow sensor configured to sense airflow of the first breathing orifice drawn through the first port.

The conserver system may further comprise a sensor fluidly associated with the second port, the second sensor being at least one selected from the group consisting of: a pressure sensor; and a flow sensor.

During the second inhalation the conserver system may couple the gas port to the first port prior to coupling the gas port to the second port.

Aspects of the various embodiments may be combined. For example, the conserver system may be arranged to carry out a method according to the first or second aspect of the invention. It will be appreciated that aspects of the various embodiments can be implemented in any convenient form. For example, various aspects may be implemented by appropriate computer programs which may be carried on appropriate carrier media which may be tangible carrier media (e.g. disks) or intangible carrier media (e.g. communications signals). Various aspects may also be implemented using suitable apparatus which may take the form of programmable computers running computer programs arranged to implement the invention.

BRIEF DESCRIPTION OF THE DRAWINGS

For a detailed description of the various embodiments, reference will now be made to the accompanying drawings in which.

DEFINITIONS AND NOMENCLATURE

Figure 1:
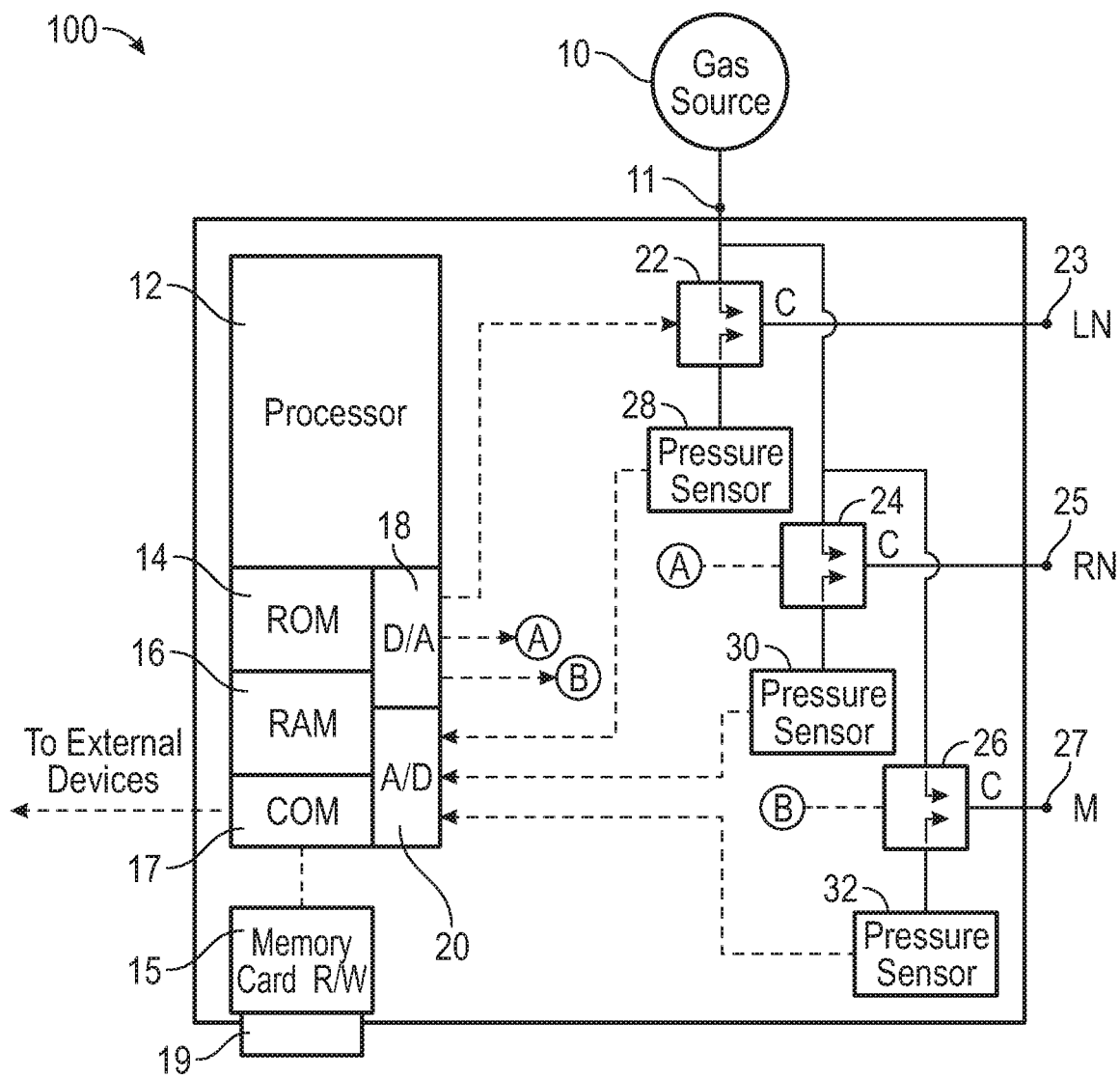
FIG. 1 shows a delivery system in accordance with at least some embodiments of the invention.

Certain terms are used throughout the following description and claims to refer to particular system components. This document does not intend to distinguish between components that differ in name but not function.

"Prescription titration volume" shall mean a volume of therapeutic gas provided at each inhalation, and shall not mean that the prescription titration volume is divided among a plurality of breaths.

"Nares" shall mean the nostrils of a patient.

"Nare" shall mean a single nostril of a patient, and is the singular of "nares."

"Flow state of breathing orifices" shall refer to a flow state of a set of breathing orifices at a particular point in time. For example, considering only the nares of a patient as the set of breathing orifices, each naris can be open to flow (designated as "O" below) or blocked to flow (designated as "B" below), and thus the flow state of the breathing orifices in the example set being the left nare and the right nare (in that order) may take any one of the following states: {O, O}, {O, B}, {B, O}, and {B, B}. Similarly, in a set being the left nare, the right nare, and mouth (in that order) the flow state may take any one of the following flow states: {O, O, O}, {O, B, O}, {B, O, O}, {B, B, O}, {O, O B}, {O, B, B}, and {B, O, B}.

The bolus delivery location control described in this specification is based on sensing whether breathing orifices are open to flow, and ensuring that substantially only the prescription titration volume is provided in spite of changes in the flow state of breathing orifices of a patient. Related-art devices may implement a pulse oximetry device to measure oxygen saturation in the blood stream, and actively change the amount of therapeutic gas provided to keep oxygen saturation in the blood stream in a predetermined range. However, for purposes of this specification and claims, a change in the amount of therapeutic gas provided responsive directly to oxygen saturation in the blood stream as measured by a pulse oximetry device shall be considered a change in the prescription titration volume, and not delivery location control to ensure that a previously existing prescription titration volume is provided in spite of changes in the flow state of the breathing orifices.

"Delivering the prescription titration volume of therapeutic gas to the patient" shall mean delivering substantially only the prescription titration volume. For purposes of this specification and claims, delivering a volume greater than the prescription titration volume shall not be considered to include or encompass delivering the prescription titration volume. Stated otherwise, "delivering the prescription titration volume of therapeutic gas to the patient" shall not be construed to mean delivering at least the prescription titration volume.

"Substantially", in relation to a recited volume, shall mean within +/−10% of the recited volume.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct electrical or mechanical connection. Thus, if a first device couples to a second device, that connection may be through a direct connection, or through an indirect connection via other devices and connections.

Various devices or other components in this disclosure may be described or claimed as "configured to" perform a task or tasks. In such contexts, "configured to" is used to connote structure by indicating that the device/component(s) include structure (e.g., circuitry, physical attributes) that perform those task or tasks during operation. As such, the device/component can be said to be configured to perform the task even when the specified device/component is not currently operational (e.g., is not on). The devices/components used with the "configured to" language include hardware—for example, circuits, memory storing program instructions executable to implements the operation, etc. Reciting that a device/component is "configured to" perform one or more tasks is expressly intended not to invoke 35 U.S.C. § 112(f) for that unit/circuit/component.

DETAILED DESCRIPTION

The following discussion is directed to various embodiments. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be an example of the embodiment, and not intended to intimate that the scope of the disclosure, including the claims, is limited to that embodiment.

The various embodiments are directed to delivery of therapeutic gas by way of bolus control. More particularly, the various embodiments control on a breath-to-breath basis the location of bolus delivery and bolus volume based on the flow state of breathing orifices of the patient. The various methods and systems described in this specification were developed in the context of addressing shortcomings of related-art devices in providing therapeutic gas to a patient. The specification starts with a brief description of operation of therapeutic gas delivery systems of the related art, and then discusses a study that highlights shortcomings of operation of the related-art systems.

The inventors of the present specification are also co-inventors of U.S. Pat. No. 7,007,692 titled "Method and system of sensing airflow and delivering therapeutic gas to a patient" (hereafter the '692 Patent), which patent is incorporated by reference herein as if reproduced in full below. The '692 Patent contemplates individually sensing airflow of the breathing orifices (e.g., by a pressure sensor, or a flow sensor) and preferentially delivering therapeutic gas to the breathing orifice or orifices that have airflow. In some cases, the delivery is Boolean in the sense that if airflow is detected, then therapeutic gas is delivered. In other cases, the '692 Patent discusses delivering therapeutic gas in proportion to airflow into the respective breathing orifice (see, e.g., claims 5 and 6 of the '692 Patent). In this way, the '692 Patent may teach reducing waste of therapeutic gas by not attempting to deliver to a breathing orifice that cannot accept the therapeutic gas.

However, the '692 Patent does not expressly address the effects on the patient that may result from reducing delivery, or not delivering at all, to breathing orifices that are partially or fully closed to flow. That is, the '692 Patent does not expressly or impliedly contemplate the effects on the fraction of inspired oxygen ($FIO_2$) percentage (hereafter just "inspired oxygen percentage") within the lungs in situations where one or more breathing orifices are blocked to flow. The specification now turns to summarized results of a study performed regarding the effects of inspired oxygen percentage as a function of flow state of breathing orifices of the patient.

In particular, by way of a confidential study commissioned by the inventors with a Texas university, a series of relationships between inspired oxygen percentage within the lungs and the flow state of breathings orifices was determined. In particular, the study related continuous flow oxygen delivered to the nares of an anatomically correct manikin (including anatomically correct nasal passages) to inspired oxygen percentage in the lungs for different flow states of the nares (i.e., both nares open, left nare blocked, right nare blocked). The oxygen was delivered to the manikin by way of a series of dual lumen cannulas, each cannula from a different manufacturer. The following table summarizes the results.

TABLE 1

| Oxygen Flow Rate (LPM) | Inspired Oxygen Both Nares Open ($FIO_2$ %) | Inspired Oxygen Left Nare Blocked ($FIO_2$ %) | Inspired Oxygen Right Nare Blocked ($FIO_2$ %) |
| --- | --- | --- | --- |
| 0.5 | 24.7 | 24.3 | 24.9 |
| 1.0 | 27.7 | 27.2 | 27.2 |
| 1.5 | 30.4 | 29.5 | 29.5 |
| 2.0 | 33.8 | 30.5 | 31.6 |
| 2.5 | 36.1 | 31.9 | 33.6 |
| 3.0 | 38.0 | 34.3 | 35.4 |
| 3.5 | 40.4 | 34.6 | 35.3 |
| 4.0 | 40.7 | 35.4 | 36.7 |
| 4.5 | 44.2 | 35.8 | 39.3 |
| 5.0 | 45.1 | 35.8 | 39.8 |
| 5.5 | 47.3 | 36.4 | 40.5 |
| 6.0 | 48.3 | 38.1 | 42.1 |

The "Oxygen Flow Rate" is the continuous flow rate of therapeutic gas (in this case oxygen) to the nares of the manikin, with the flow split evenly between the two lumens of the cannula. The "Inspired Oxygen Both Nares Open" is the inspired oxygen percentage in the state with both nares open to flow. The "Inspired Oxygen Left Nare Blocked" is the inspired oxygen percentage in the state with the right nare open to flow, and the left nare closed to flow. And the "Inspired Oxygen Right Nare Blocked" is the inspired oxygen percentage in the state with the left nare open to flow, and the right nare closed to flow.

The specification next presents a series of scenarios referencing Table 1 to highlight shortcomings of the related art identified in the study.

Continuous Flow Scenarios

Scenario 1—Patient Titrated on 2 LPM Continuous Flow, Both Nares Open

In Scenario 1, consider that a patient is titrated using a continuous flow system during a period of time when both patient's nares are open to flow. By titration it is meant that the patient is provided oxygen at a series of differing flow rates until the patient maintains an oxygen saturation in the blood stream at or above a predetermined level (e.g., above 95%, perhaps during light exercise like walking). The flow rate that results in the predetermined oxygen saturation may then be selected by the doctor as the prescription flow rate. Further consider that in Scenario 1 the patient's prescription flow rate is set at 2 liter per minute (LPM). From Table 1 it is seen that a flow rate of 2 LPM with both nares open to flow results in an inspired oxygen percentage of 33.8%.

Humans experience what is known as "nasal cycle." That is, humans periodically experience unilateral changes in nasal resistance with a frequency of between 25 minutes and 4 hours, with an average of 2.5 hours between cycles. Thus, though both nares of a patient may be open to flow during a period of time when titration of the patient is taking place, the effect of nasal cycle may be to restrict, or close off completely, airflow through any particular nare at some point in time thereafter.

Considering Scenario 1 (titration with both nares open, 2 LPM prescription flow rate), if the patient later experiences a blockage of the left nare, Table 1 shows that in the test configuration the inspired oxygen percentage drops to 30.5% (a 3.3% drop in inspired oxygen percentage). The 30.5% inspired oxygen percentage is about the same as a 1.5 LPM flow for the unblocked state (from Table 1, 30.4%), and thus it follows that the blockage of the left nare in Scenario 1 results in the patient receiving at least 0.5 LPM too little oxygen flow, which oxygen flow is lost to atmosphere.

Another way to quantify the drop in inspired oxygen percentage is to determine how much the continuous flow of oxygen would need to increase to achieve approximately the same inspired oxygen percentage. Looking again at Table 1 it is seen than an oxygen flow rate of just under 3 LPM would be needed to maintain the higher inspired oxygen percentage in the left nare blocked state (at 3 LPM, Table 1 shows 34.3% for the left nare blocked condition). Stated otherwise, to get the same inspired oxygen percentage in the left nare blocked state would require a continuous flow of just under 3 LPM (an increase of about 1 LPM over the (non-blocked) titration prescription of 2 LPM).

Scenario 2—Patient Titrated on 3 LPM Continuous Flow, Both Nares Open

In Scenario 2, consider that a patient is titrated using a continuous flow system during a period of time when the patient's nares are both open to flow. Further consider that in Scenario 2 the patient's prescription flow rate is set at 3 LPM. From Table 1 it is seen that a flow rate of 3 LPM with both nares open to flow results in an inspired oxygen percentage of 38%.

If the patient later experiences a blockage of the left nare, Table 1 shows that the inspired oxygen percentage drops to 34.3% (a 3.7% drop in inspired oxygen percentage). The 34.3% inspired oxygen percentage is about the same as a 2.1 LPM flow for the unblocked state (from Table 1, straight interpolation between 33.8% (for 2 LPM) and 36.1% (for 2.5 LPM)), and thus it follows that the blockage of the left nare in Scenario 2 results in the patient receiving 0.9 LPM too little oxygen flow, which oxygen flow is lost to atmosphere.

Another way to quantify the drop in inspired oxygen percentage is to determine how much the continuous flow of oxygen would need to increase to achieve approximately the same inspired oxygen percentage. Looking again at Table 1 it is seen than an oxygen flow rate of just under 6 LPM would be needed to maintain the higher inspired oxygen percentage in the left nare blocked state (at 6 LPM, Table 1 shows 38.1% for the left nare blocked condition). Stated otherwise, to get the same inspired oxygen percentage in the left nare blocked state would require a continuous flow of about 6 LPM (an increase of about 3 LPM over the (non-blocked) titration prescription of 3 LPM).

Scenario 3—Patient Titrated on 3 LPM Continuous Flow, Left Nare Blocked

In Scenario 3, consider that a patient is titrated using a continuous flow system during a period of time when the patient's left nare is blocked to flow but the right nare is open to flow. Further consider that in Scenario 3 the patient's prescription flow rate is set at 3 LPM. From Table 1 it is seen that a flow rate of 3 LPM with the left nare blocked results in an inspired oxygen percentage of 34.3%.

If the patient later experiences a flow state where both nares are open to flow, Table 1 shows that the inspired oxygen percentage increases to 38% (a 3.7% increase in inspired oxygen percentage). The 34.3% inspired oxygen percentage is about the same as a 2.1 LPM flow for the unblocked state (from Table 1, straight interpolation between 33.8% (for 2 LPM) and 36.1% (for 2.5 LPM)), and thus it follows that the opening of the left nare in Scenario 3 results in the patient receiving 0.9 LPM too much oxygen flow.

Scenario 4—Patient Titrated on 6 LPM Continuous Flow, Left Nare Blocked

In Scenario 4, consider that a patient is titrated using a continuous flow system during a period of time when the patient's left nare is blocked to flow but the right nare is open to flow. Further consider that in Scenario 4 the patient's prescription flow rate is set at 6 LPM. From Table 1 it is seen that a flow rate of 6 LPM with the left nare blocked results in an inspired oxygen percentage of 38.1%.

If the patient later experiences a flow state where both nares are open to flow, Table 1 shows that the inspired oxygen percentage increases to 48.3% (a 10.2% increase in inspired oxygen percentage). The 38.1% inspired oxygen percentage is about the same as a 3 LPM flow for the unblocked state, and thus it follows that the opening of the left nare in Scenario 4 results in the patient receiving 3 LPM too much oxygen flow.

Bolus Flow Scenarios

The specification now turns conserver or bolus flow scenarios. In particular, in continuous flow situations the patient is provided a continuous flow of oxygen at the prescription flow rate; however, oxygen delivered during exhalation (and the rest period between inhalation and exhalation) provides no therapeutic value. Moreover, even oxygen that is inhaled during later portions of an inspiration may not travel sufficiently far into the lungs to provide therapeutic value. Thus, in some situations (e.g., mobile oxygen delivery from a bottle of limited volume) a patient is supplied therapeutic gas in a conserver mode, where a bolus of therapeutic gas is provided only at the beginning of each inhalation. Published relationships indicate that for every 1 LPM of continuous flow prescription the equivalent bolus delivery is 16.5 milliliters (ml) at the beginning of the inhalation. The following scenarios highlight that, even in the case of bolus delivery, nasal cycle may result in a patient receiving too little therapeutic gas (and the balance being wasted), or the patient receiving too much therapeutic gas. Note that it is possible to titrate a patient with a conserver delivery system; however, to better tie the following scenarios to the previous scenarios it will be assumed that the patient is titrated with a continuous flow system, and the relationship given above (i.e., 16.5 ml bolus for every 1 LPM continuous flow prescription) is used to correlate to the bolus delivery system.

Scenario 5—Patient Titrated on 2 LPM Continuous Flow, Both Nares Open

In Scenario 5, consider that a patient is titrated using a continuous flow system during a period of time when the patient's nares are both open to flow. Further consider that in Scenario 5 the patient's prescription flow rate is set at 2 liter per minute (LPM). Thus, Scenario 5 is related to Scenario 1. However, using the relationship given above, for a 2 LPM prescription flow rate, in conserver or bolus flow mode 33 ml is provided at each inhalation, being 16.5 ml provided to each nare by way of a bifurcated nasal cannula. If the patient later experiences a blockage of the left nare, the 16.5 ml provided to the left nare is not inhaled by the patient. The patient not only gets too little therapeutic gas flow, the 16.5 ml provided to the blocked nare is wasted to atmosphere.

Considered from the standpoint of continuous flow, the loss of 16.5 ml of flow to the patient equates to a drop in continuous flow equivalent of about 1 LPM. This drop in continuous flow equivalent is about the same as the drop in Scenario 1.

Scenario 6—Patient Titrated on 3 LPM Continuous Flow, Left Nare Blocked

In Scenario 6, consider that a patient is titrated using a continuous flow system during a period of time when the patient's left nare is blocked to flow but the right nare is open to flow. Further consider that in Scenario 6 the patient's prescription flow rate is set at 3 LPM. Thus, Scenario 6 is related to Scenario 3. However, using the relationship given above, for a 3 LPM prescription flow rate, in conserver or bolus flow mode 49.5 ml is provided at each inhalation, being 24.75 ml provided to each nare by way of a bifurcated nasal cannula. However, because the left nare is blocked, only about 24.75 ml of therapeutic gas makes its way to the patient's lungs during each inhalation. If the patient later experiences a flow state where both nares open to flow, the patient receives the full 49.5 ml during each inhalation. The patient thus receives too much therapeutic gas flow.

Considered from the standpoint of continuous flow, the additional 24.75 ml of flow to the patient equates to an increase in continuous flow equivalent of about 1.5 LPM. This increase in continuous flow equivalent is about the same as the increase in Scenario 3.

Summarizing the Scenarios

From the continuous flow study results, and the related bolus flow scenarios, it is seen that merely ceasing delivery to a breathing orifice that has become blocked since titration, while saving therapeutic gas, may result in providing too little therapeutic gas to the patient. Likewise, delivering therapeutic gas to a breathing orifice that has opened since titration may result in provide too much therapeutic gas to the patient. The various embodiments of the current disclosure, discussed in detail below, address (at least in part) the shortcomings of identified.

Before proceeding, it is noted that the study results of Table 1 represent a situation of a particular size and arrangement of nasal passages (in the manikin of the study). Humans come in many shapes and sizes, and it is acknowledged that the specific numbers of Table 1 are not necessarily accurate for all humans; however, the study results can and do represent trends in changes in inspired oxygen percentage for most if not all humans, and thus the inventors respectfully submit that such results are applicable to the human population as a whole.

Example Systems

With the study results and the shortcomings of the related-art highlighted based on the study results, the specification now turns to a description of various embodiments which address, at least in part, the shortcomings noted, starting with a description of systems which may be used to provide therapeutic gas.

FIG. 1 shows a delivery system 100 in accordance with at least some embodiments. The delivery system 100 may be coupled to a therapeutic gas source 10 by way of a gas port 11. The therapeutic gas source 10 may be any suitable source of therapeutic gas, such as a portable cylinder, an oxygen concentration system or a permanent supply system as in a hospital. The delivery system also couples to a patient (not shown) by any of a variety of devices and systems by way of a variety of ports, such as nare ports 23, 25 and an oral port 27. For example, the delivery system 100 may couple to a patient's nares by way of a nasal cannula. In accordance with at least some embodiments, the delivery system 100 monitors patient breathing and delivers therapeutic gas to a left nare (LN), right nare (RN) and/or to the mouth (M) of the patient when the nares/mouth is/are open to flow.

In accordance with at least some embodiments, the delivery system 100 comprises both electrical components and mechanical components. In order to differentiate between electrical connections and mechanical connections, FIG. 1 (and the remaining figures) illustrate electrical connections between components with dashed lines, and fluid connections, e.g. tubing connections between devices, with solid lines. The delivery system 100 of FIG. 1 comprises a processor 12. The processor 12 may be a microcontroller, and therefore the microcontroller may be integral with read-only memory (ROM) 14, random access memory (RAM) 16, a digital-to-analog converter (D/A) 18, and an analog-to-digital converter (A/D) 20. The processor 12 may further comprise communication logic 17, which enables the system 100 to communicate with external devices. The communication logic 17 may, for example, transfer stored data about a patient's breathing patterns to external agents, or write the data about the patient's breathing patterns to a removable memory card, such as a memory card read/write device 15 and memory card 19 (e.g., a secure digital (SD) nonvolatile memory card). Although a microcontroller may be used, in alternative embodiments the processor 12 may be implemented by a stand-alone central processing unit in combination with individual RAM, ROM, communication D/A and A/D devices.

The ROM 14 stores instructions executable by the processor 12. In particular, the ROM 14 may comprise a software program that implements the various embodiments discussed herein. The RAM 16 may be the working memory for the processor 12, where data may be temporarily stored and from which instructions may be executed. Processor 12 may couple to other devices within the preferential delivery system by way of A/D converter 20 and D/A converter 18.

The example delivery system 100 also comprises three-port valve 22, three-port valve 24, and three-port valve 26. In accordance with various embodiments, each of these three-port valves may be a five-volt solenoid operated valve that selectively couples one of two ports to a common port (labeled as C in the drawings). Three-port valves 22, 24 and 26 may be Humprey Mini-Mizers having part No. D3061, such as may be available from the John Henry Foster Co., or equivalents. By selectively applying voltage on a digital output signal line coupled to the three-port valve 22, the processor 12 may be able to: couple gas from the gas source 10 to the common port and therefore to the exemplary left nare; and couple the pressure sensor 28 to the common port and therefore the exemplary left nare. Likewise, the three-port valve 24, under command of the processor 12, may: couple gas from the gas source 10 to the common port and therefore the exemplary right nare; and couple the pressure sensor 30 to the common port and therefore the exemplary right naris. Further still, three-port valve 26 under command of the processor 12, may: couple gas from the gas source 10 to the common port and therefore the patient's mouth; and couple the pressure sensor 32 to the common port and therefore the mouth. When the pressure sensors 28, 30 and 32 are coupled to the respective common ports, the processor 12 may read (through corresponding A/D converter 20 input signal lines) pressures indicative of airflow by the patient through the respective breathing orifice. In alternative embodiments, the pressure sensors 28, 30, and 32 couple to the common ports of the valves 22, 24, and 26, respectively, if the pressure sensors can withstand the pressure of the therapeutic gas during bolus delivery without damage. Regardless of the precise placement, the processor 12 may be able to determine when the patient is inhaling, and an indication of how much of the air drawn by the patient flows through each of the monitored breathing orifices.

Consider a situation where the delivery system 100 couples to the nares of the patient by way of a bifurcated nasal cannula. As the patient inhales, outlet ports in the nasal cannula proximate to the openings of each nare experience a drop in pressure. The drop in pressure may be sensed through the nasal cannula and associated hosing by each of the pressure sensors 28 and 30. Likewise, a sensing and delivery tube may be placed proximate to the patient's mouth, and thus pressure sensor 32 may detect an oral inspiration by the patient. In accordance with various embodiments, the delivery system 100 senses whether a patient has airflow through a monitored breathing orifice, and delivers therapeutic gas to the location or locations in such a manner to ensure the patient's full prescription titration volume is delivered in spite of changes in the flow state of the breathing orifices of the patient.

Still considering the situation where the patient couples to the delivery system 100 by way of a bifurcated nasal cannula and a separate sensing and delivery tube for the mouth, if there is no obstruction to inhalation in either of the nares or the mouth, therapeutic gas may be provided to any one or a combination of the nares and the mouth. Should the nasal cannula become partially dislodged, therapeutic gas may be provided only to the nare where the outlet port of the nasal cannula is still in operational relationship to the nare. Should the patient's nares become congested or blocked, therapeutic gas may be provided to the nare that is open.

In accordance with various embodiments, the delivery system 100 operates in a conserve mode, delivering a bolus of gas during each inhalation of the patient. Consider for purposes of explanation the left nare port 23 illustrated in FIG. 1, as well as its associated three-port valve 22 and pressure sensor 28. Prior to an inhalation, the three-port valve 22 may couple the pressure sensor to the common port of three-port valve 22 and therefore the left nare. As the patient starts an inhalation, as sensed by the pressure sensor 28 and read by processor 12, the three-port valve 22 changes valve position (as commanded by processor 12) and couples the therapeutic gas source 10 to the common port (and effectively blocks the pressure sensor 28 from the common port). The therapeutic gas flows to the exemplary left nare for a period of time to provide the prescription titration volume (or portion thereof). When the desired bolus volume has been delivered (e.g., as function of flow rate of the therapeutic gas and time) the processor 12 commands the three-port valve 22 to its original state, again fluidly coupling the pressure sensor 28 to the left naris. During exhalation, again sensed by pressure sensor 28, the three-port valve 22 remains in the valve position coupling the pressure sensor to the common port, and therefore no therapeutic gas is delivered. The exemplary process is equally applicable to three-port valve 24 and pressure sensor 30 in operational relationship to the right nare, as well as three-port valve 26 and pressure sensor 32 in operational relationship to the patient's mouth. Thus, the delivery system 100 detects whether the nares and/or mouth are open to therapeutic gas flow with each inspiration. In the event an inspiration on any particular delivery path is not detected, indicating a blockage or other gas delivery problem, the delivery system 100 refrains from providing therapeutic gas to that breathing orifice, and increases the volume to the remaining breathing orifices to ensure the patient's prescription titration volume is provided.

Figure 2A:
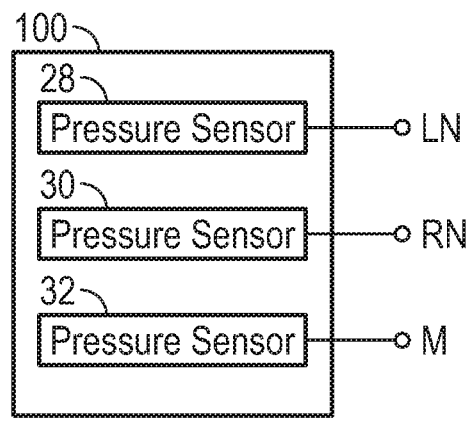
FIG. 2A shows, in shorthand notation, the system of FIG. 1.
Figure 2B:
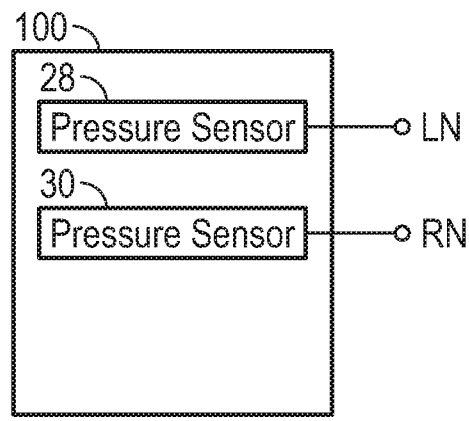
FIG. 2B shows an alternative embodiment of the system of FIG. 1.
Figure 2C:
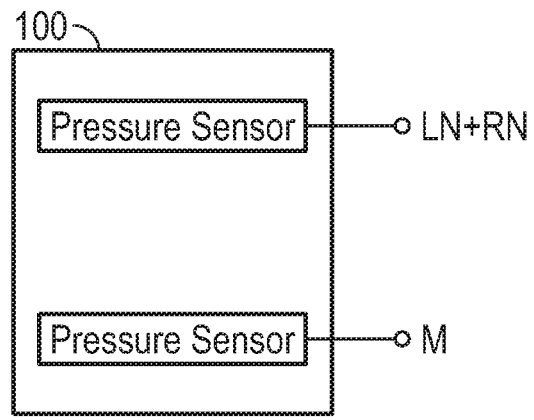
FIG. 2C shows yet another alternative embodiment of the system of FIG. 1.

FIG. 2A illustrates the delivery system 100 of FIG. 1 in a shorthand notation, showing only pressure sensors 28, 30 and 32 coupled to the respective breathing orifices. FIG. 2B illustrates alternative embodiments monitoring and delivering therapeutic gas only to the nares of a patient. In the embodiments of FIG. 2B, if both the left nare and right nare are open to flow the delivery system 100 may deliver therapeutic gas to either nare, to both nares, or in an alternating fashion, but in any event the volume delivered to the open nare(s) is controlled to ensure the patient receives the prescription titration volume. In the event that either the left or right nare become clogged or blocked, or if the sensing and delivery tubing (such as a nasal cannula) become dislodged, the delivery system provides the entire prescription titration volume to the nare where airflow is sensed. FIG. 2C illustrates alternative embodiments where two pressure sensors are used, but in this case only one pressure sensor is associated with the nares, and the second pressure sensor is associated with the mouth. In the embodiments of FIG. 2C, a patient may utilize a single lumen cannula associated with the nares and a second sensing and delivery tube associated with the mouth. The delivery system 100 may thus selectively provide therapeutic gas to the nares and/or to the mouth. In the event that either of the nares as a group or the mouth become blocked or otherwise unavailable for inspiration, the delivery system 100 provides the full prescription titration volume to the breathing orifice through which inhalation takes place.

Figure 3:
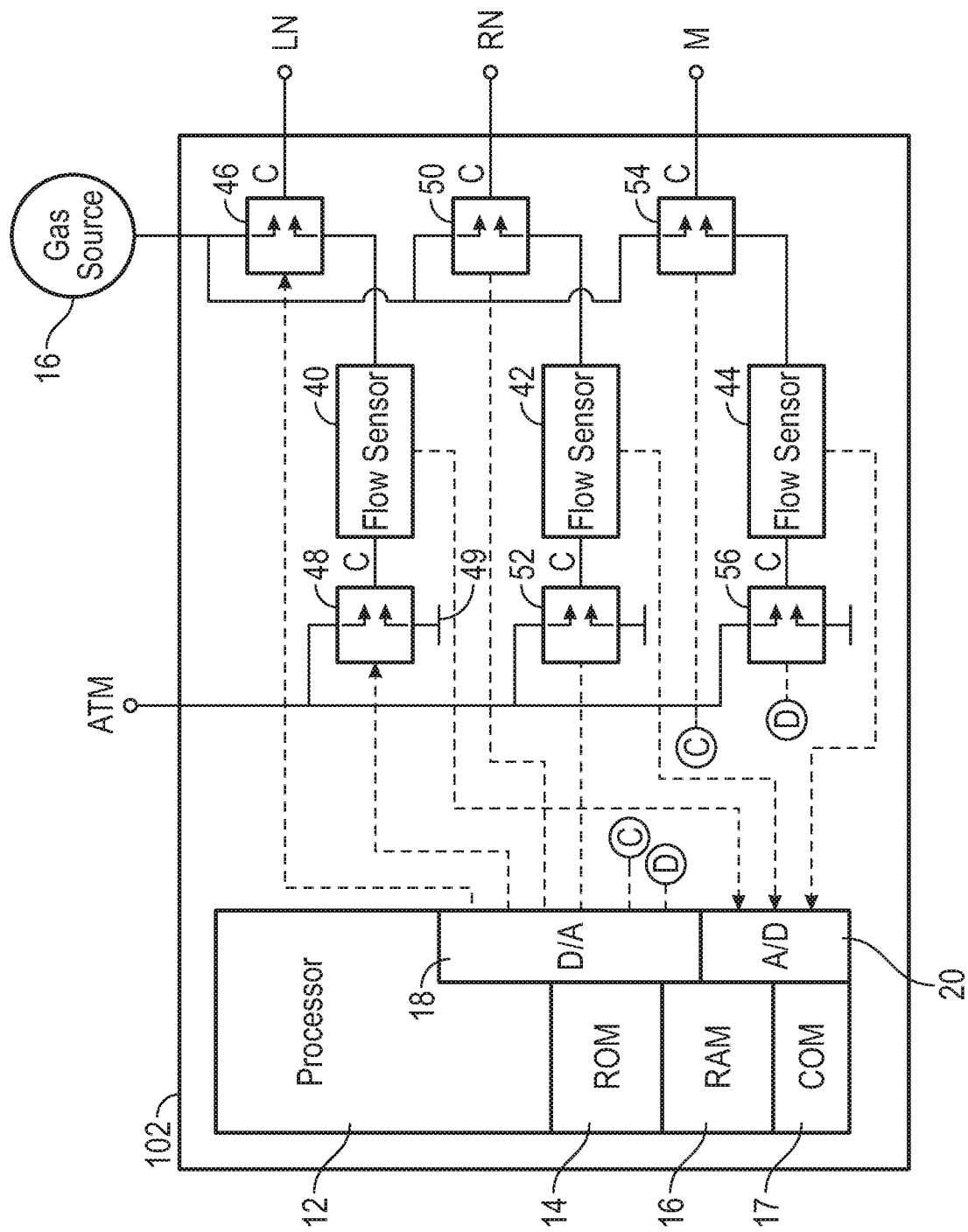
FIG. 3 shows a delivery system in accordance with alternative embodiments.

FIG. 3 illustrates a delivery system 102 constructed in accordance with alternative embodiments. Like the system of FIG. 1, the delivery system 102 comprises a processor 12, possibly in the form of a microcontroller, comprising ROM 14, RAM 16, a D/A converter 18, and an ND converter 20. The delivery system 102 may also enable external communications through the communication logic 17 and data writing to a memory card reader/writer, but those abilities are not shown in FIG. 3 so as not to further complicate the figure. In the system of FIG. 3, rather than using pressure sensors, flow sensors 40, 42 and 44 are used. Thus, the delivery system 102 may sense a portion of the flow associated with each breathing orifice. Consider for purposes of explanation the flow sensor 40 and three-port valves 46, 48 coupled to the left nare. Three-port valve 46, under command of the processor 12, may: couple the gas source 10 to the common port and therefore the exemplary left nare; and couple the flow sensor 40 to the common port and therefore the exemplary left nare. Thus, during a period of time when the delivery system 102 provides therapeutic gas to the left nare, the three-port valve 46 provides the therapeutic gas to the left nare and blocks the flow sensor. In a second valve position, the three-port valve 46 fluidly couples the flow sensor to the common port and therefore the exemplary left nare. However, flow sensor 40 may not be operational until gas can flow through the sensor. Three-port valve 48, in a first valve position, couples the flow sensor 40 to an atmospheric vent (marked ATM in the drawing), thus allows air to flow through the flow sensor for measurement purposes. The three-port valve 48, in a second valve position, couples to a blocked port 49. Consider for purposes of explanation a delivery system 102 operating in a conserve mode. After a bolus has been delivered, the three-port valve 46 may change valve positions, thus fluidly coupling the flow sensor 40 to the common port and the exemplary left nare. If the flow sensor 40 outlet is not blocked, a portion of the therapeutic gas may reverse flow through the flow sensor 40 and out the atmospheric vent. Three-port valve 48 (as well as corresponding three-port valves 52 and 56) may be used to temporarily block reverse flow and loss of therapeutic gas, i.e. the valves may remain in a position that blocks flow for about 300 milliseconds after therapeutic gas delivery has stopped by a change of valve position by upstream three-port valves 46, 50 and 54. After the expiration of the period of time of possible reverse flow has ended, one or more of the three-port valves 48, 52 and 56 may change valve positions, thus allowing the flow sensors to sense airflow. The description with respect to the three-port valves 46, 48 and flow sensor 40 for the left nare is equally applicable for the corresponding structures for the right naris and mouth.

Figure 4A:
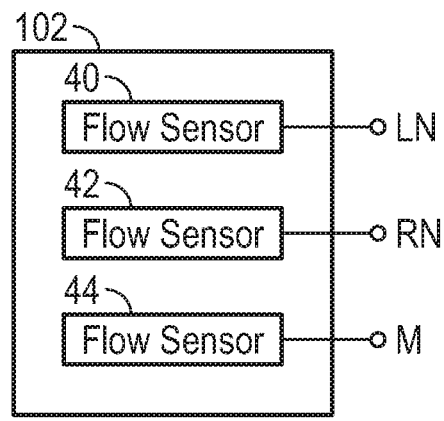
FIG. 4A shows, in shorthand notation, the system of FIG. 3.
Figure 4B:
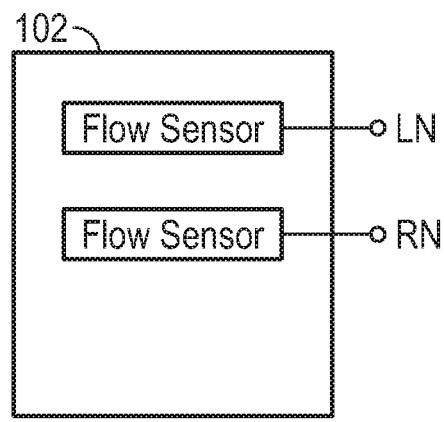
FIG. 4B shows an alternative embodiment of the system of FIG. 3.
Figure 4C:
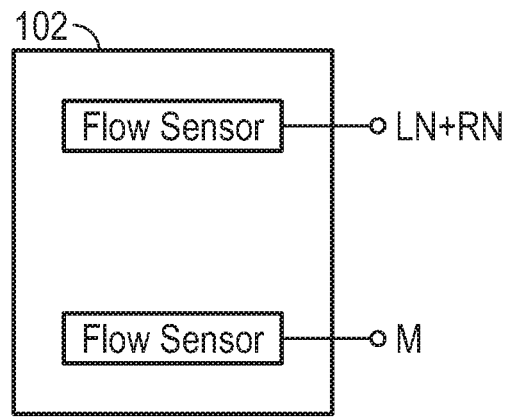
FIG. 4C shows yet another alternative embodiment of the system of FIG. 3.

FIG. 4A illustrates the delivery system 102 of FIG. 3 in a shorthand notation, showing only flow sensors 40, 42 and 44 coupled to their respective breathing orifice. FIG. 4B illustrates alternative embodiments where only a patient's nares are used for sensing and delivery. In the embodiments of FIG. 4B, if both the left nare and right nare are open to flow the delivery system 102 delivers therapeutic gas to either nare, to both nares, or in an alternating fashion, but in any event the volume delivered to the open nare(s) is controlled to ensure the patient receives the prescription titration volume. In the event that either the left or right nare become clogged or blocked, or if the sensing and delivery tubing (such as a nasal cannula) become dislodged, the delivery system provides the entire prescription titration volume to the nare where airflow is sensed. FIG. 4C illustrates further alternative embodiments where two flow sensors are used, but in this case only one flow sensor is associated with the nares, and the second flow sensor associated with the mouth. In the embodiments of FIG. 4C, a patient may utilize a single lumen cannula associated with the nares, and a second sensing and delivery tube associated with the mouth. The delivery system 102 may thus selectively provide therapeutic gas to the nares and/or the mouth. In the event that either of the nares as a group or the mouth become blocked or otherwise unavailable for inspiration, the delivery system 102 provides the full prescription titration volume to the breathing orifice through which inhalation takes place.

Figure 5:
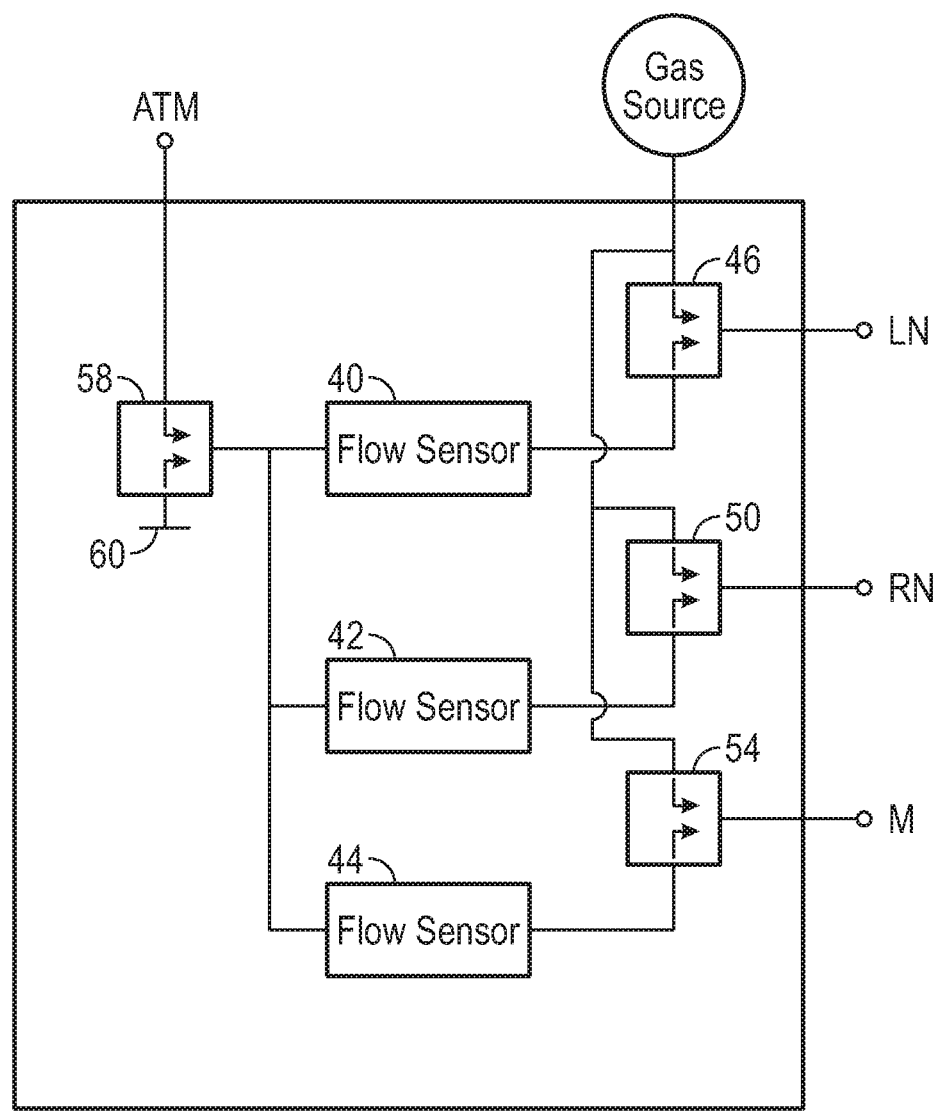
FIG. 5 shows an alternative embodiment of the system of FIG. 3 using fewer three-port valves.

FIG. 5 illustrates alternative embodiments utilizing flow sensors, but reducing the number of three-port valves used. The electrical components have been omitted from FIG. 5 for purposes of clarity. In particular, FIG. 5 illustrates that the three three-port valves 48, 52 and 56 of FIG. 3 may be replaced by a single three-port valve 58. Blocking reverse flow through the flow sensors in the embodiments of FIG. 5 may be accomplished by single three-port valve 58. Relatedly, opening the second port of each of the flow sensors to the atmosphere vent so that flow may be detected may likewise be accomplished with a single three-port valve 58.

Figure 6:
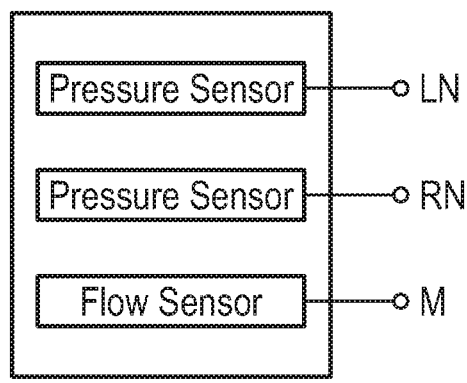
FIG. 6 illustrates, in shorthand notation, a delivery system using multiple types of sensing devices.

The example systems need not have only one type of sensor. In yet still further cases, a single system may have both pressure sensors and flow sensors. For example, the size of the nares in relation to airflow drawn through nares lends itself well to detection using pressure sensors. However, given the size of the mouth (when open) in relation to the amount of airflow drawn into the mouth (particularly when the nares are also open flow), better sensing may be achieved using a flow sensor. FIG. 6 shows, in the shorthand notation of FIGS. 2A-C and 4A-C, a system in which pressure sensors are used for sensing at the nares, and a pressure sensor is used for sensing at the mouth.

Bolus Volume Control

The specification now turns to bolus control. As described above, the systems in accordance with various embodiments control the bolus volumes such that the patient receives the full prescription titration volume regardless of the changing flow states of the breathing orifices. One bolus control implementation involves controlling delivery time to each breathing orifice. In particular, and considering the system 100 of FIG. 1 as an example, the gas source 10 provides therapeutic gas at a particular pressure. In the case of a therapeutic gas bottle, a pressure regulator may provide a relatively constant therapeutic gas pressure (in spite of the loss of pressure in the bottle with continued use). In the case of use of the system 100 in a hospital, the gas source may be therapeutic gas available in the room of the patient, again at a predetermined and controlled pressure. To control the volume of therapeutic gas delivered to each breathing orifice, an amount of time respective three-port valves 22, 24, and 26 couple the gas source to the ports 23, 25, and 27, respectively, may be controlled. Considering the three-port valve 22 and the left nare port 23 as an example. Depending on the size of tubing within the systems 100, and the size and length of the tubing fluidly coupling the left nare port 23 to the patient, the three-port valve 22 is opened for period of time to enable the volume of therapeutic gas to flow to the patient—longer times result in greater volume, and shorter times result in lesser volumes.

Consider a situation where a patient is titrated during a period of time when both the first and second nares are open to flow. The titration results in determining a prescription titration volume (e.g., in milliliters per inhalation for bolus delivery). During periods of time when both nares are open to flow, the respective three port valves are opened for a first amount of time to equally split the overall prescription titration volume between the two nares. Now consider that the left nare becomes blocked to flow. In the example situation, related-art devices merely refrained from providing therapeutic gas to the blocked nare, and only flowed therapeutic gas to the open nare for the same first amount of time used in the case where both nares were open to flow. Thus related-art devices do not account for lowering of inspired oxygen percentage in the case where one nare becomes blocked. In accordance with the example systems and methods, and in the example situation where titration takes place with both nares open to flow but later one nare becomes blocked, the amount of therapeutic gas to the open nare is increased by increasing the amount of time the three-port valve enables therapeutic gas flow to the open nare. Again, in this way the patient receives the full prescription titration volume in spite of the change in the flow state of the breathing orifices of the patient.

Now consider the reverse situation—the patient is titrated with one nare blocked, but later the both nares open to flow. During periods of time only one nare is open to flow, the three-port valve associated with the open nare is opened for a first amount of time to provide the full prescription titration volume to the open nare. Now consider that the formerly blocked nare opens to flow. In the example situation, related-art devices merely provide therapeutic gas to the newly opened nare for the first amount of time. Thus related-art devices do not account for the increase of inspired oxygen in the case where one nare is initially blocked but then later opens to flow. In accordance with the example systems and methods, and in the example situation where titration takes place with only one nare open to flow but later both nares are open to flow, the amount of therapeutic gas to the originally open nare is decreased by decreasing the amount of time the three-port valve enables therapeutic gas flow to the formerly open nare, and the newly opened nare is provided therapeutic gas for an equal amount of time. Again, in this way the patient receives only the full prescription titration volume in spite of the change in the flow state of the breathing orifices of the patient.

In other cases, the volume of therapeutic gas provided to a breathing orifice may be controlled in other ways, such as by pulse-width modulation of the respective three-port valves. Consider again the situation where a patient is titrated during a period of time when both the first and second nares are open to flow, and later one nare becomes blocked to flow. During periods of time when both nares are open to flow, the respective three-port valves may be pulse-width modulated at a corresponding first duty cycle to equally split the overall prescription titration volume between the two nares. When the one nare becomes blocked to flow, no flow is provided to the blocked nare, and the amount of therapeutic gas to the open nare is increased by increasing the duty cycle of the three-port valve enables therapeutic gas flow to the open nare. Again, in this way the patient receives the full prescription titration volume in spite of the change in the flow state of the breathing orifices of the patient.

Now consider the reverse situation—the patient is titrated with one nare blocked, but later the both nares open to flow. During periods of time when only one nare is open to flow, the three-port valve associated with the open nare is pulse-width modulated at a first duty cycle to provide the full prescription titration volume to the right nare. Now consider that the formerly blocked nare opens to flow. When the newly opened nare becomes open to flow, and the amount of therapeutic gas to the originally open nare is decreased by lowering the duty cycle duty cycle of the three-port valve associated with the originally open nare, and providing therapeutic gas to the newly open left nare at the lowered duty cycle. Again, in this way the patient receives only the full prescription titration volume in spite of the change in the flow state of the breathing orifices of the patient.

In the pulse-width modulation cases, it was assumed that the delivery time (i.e., the amount of time in which pulse-width modulation is performed) is held constant; however, in yet still further cases any combination of delivery time and/or pulse-width modulation duty cycle may be used to control the volume of therapeutic gas provided to each breathing orifice to ensure the overall prescription titration volume is delivered to the patient in spite of changing flow states of the breathing orifices of the patient.

Figure 7:
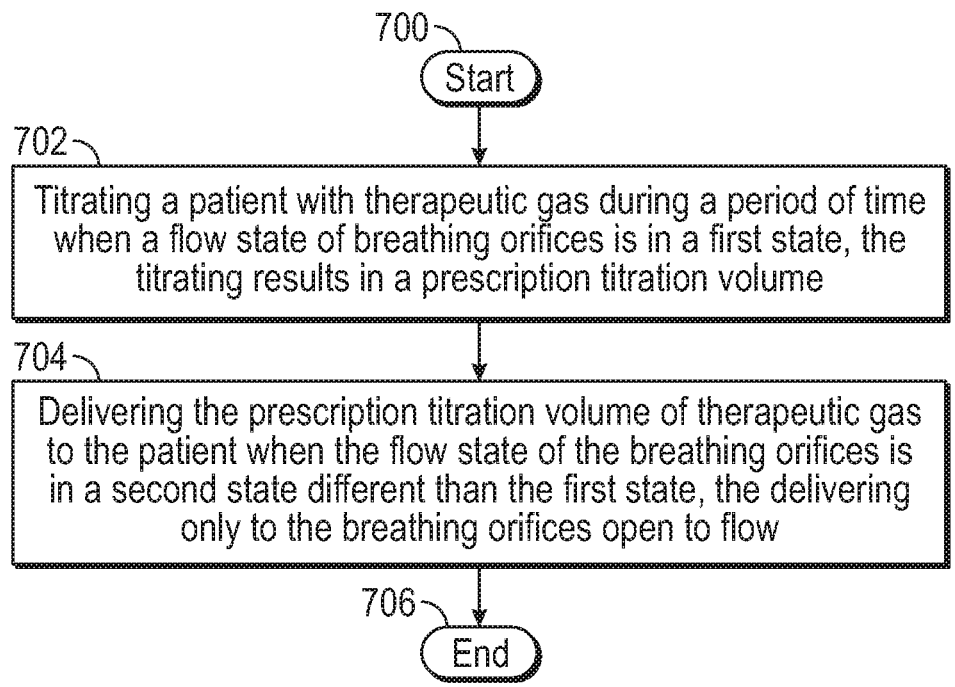
FIG. 7 shows a method in accordance with at least some embodiments.

FIG. 7 shows a flow diagram of a method in accordance with at least some embodiments, some of which may be performed by software executing on a processor associated with the delivery system. In particular, the method starts (block 700) and proceeds to titrating a patient with therapeutic gas during a period of time when a flow state of breathing orifices is in a first state, the titrating results in a prescription titration volume (block 702). The method then involves delivering the prescription titration volume of therapeutic gas to the patient when the flow state of the breathing orifices is in a second state different than the first state, the delivering only to the breathing orifices open to flow (block 704). Thereafter the method ends (block 706).

Figure 8:
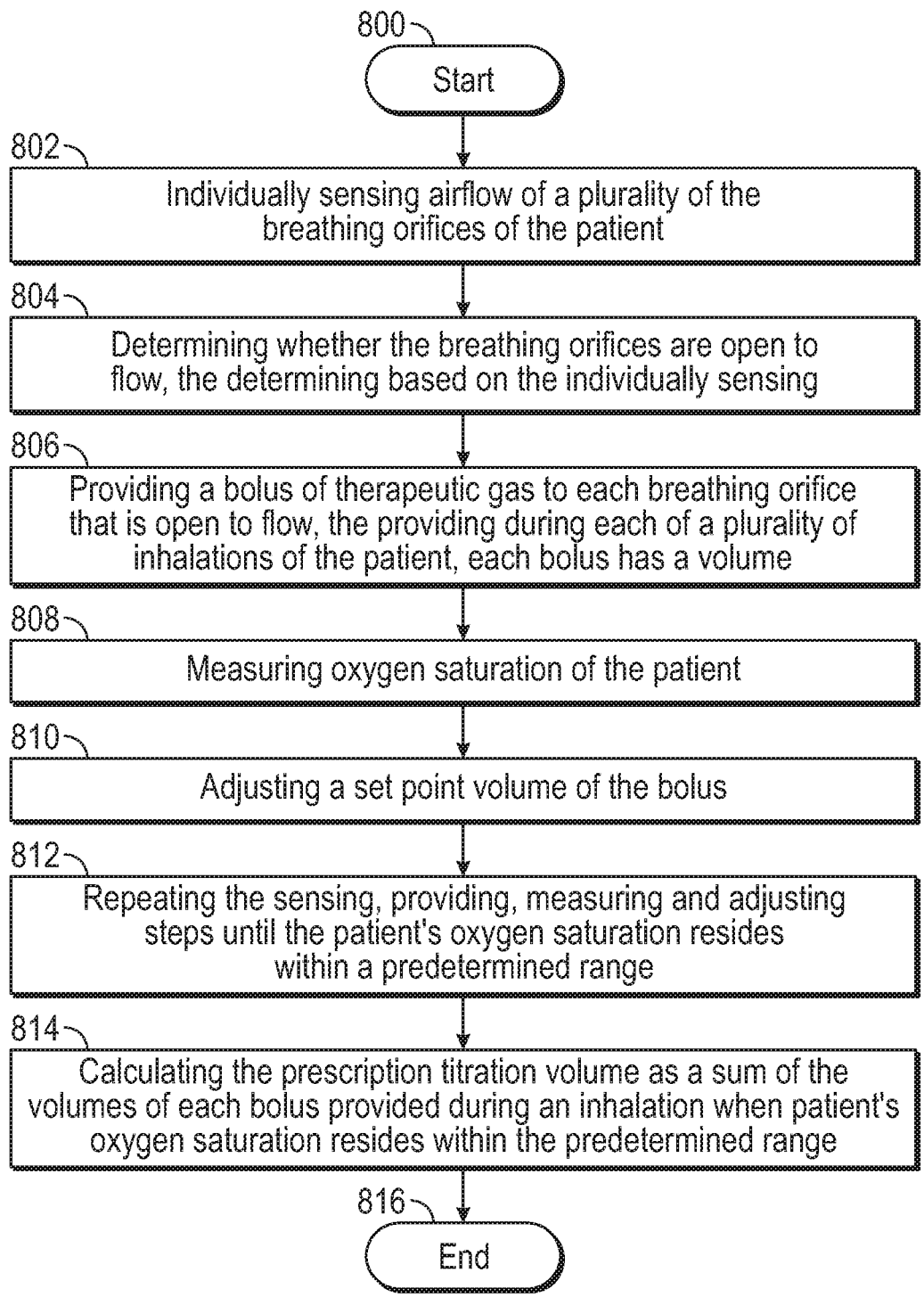
FIG. 8 shows a method in accordance with at least some embodiments.

FIG. 8 shows a method in accordance with at least some embodiments, some of which may be performed by software executing on a processor associated with the delivery system. In particular, the method starts (block 800) and proceeds to: individually sensing airflow of a plurality of the breathing orifices of the patient (block 802); determining whether the breathing orifices are open to flow, the determining based on the individually sensing (block 804); providing a bolus of therapeutic gas to each breathing orifice that is open to flow, the providing during each of a plurality of inhalations of the patient, each bolus has a volume (block 806); measuring oxygen saturation of the patient (block 808); adjusting a set point volume of the bolus (block 810); repeating the sensing, providing, measuring and adjusting steps until the patient's oxygen saturation resides within a predetermined range (block 812); and calculating the prescription titration volume as a sum of the volumes of each bolus provided during an inhalation when patient's oxygen saturation resides within the predetermined range (block 814). Thereafter the method ends (block 816).

Figure 9:
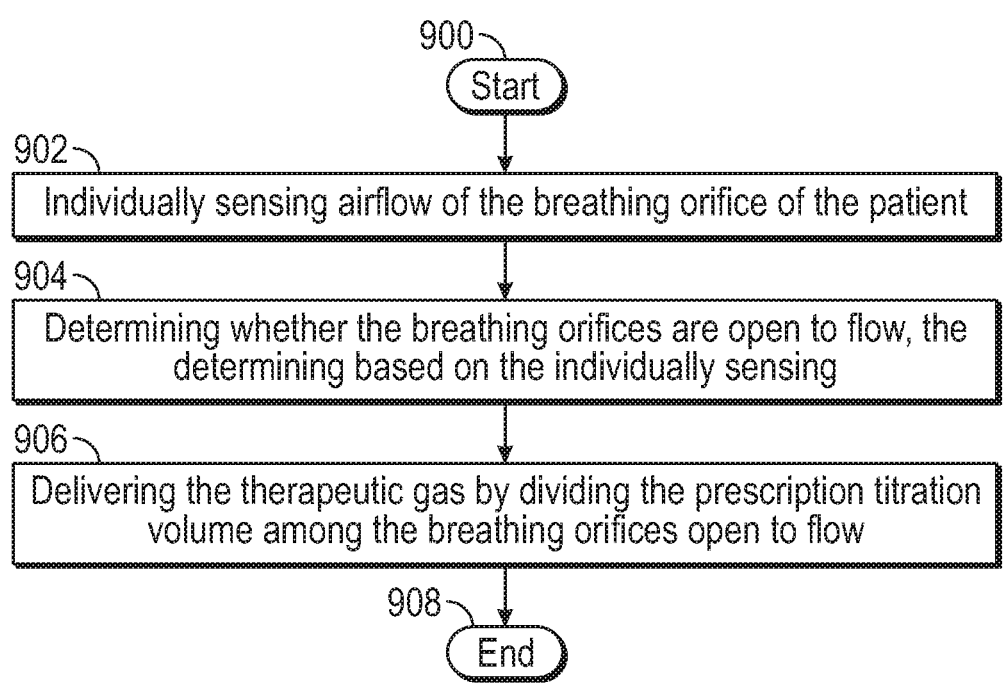
FIG. 9 shows a method in accordance with at least some embodiments.

FIG. 9 shows a method in accordance with at least some embodiments, some of which may be performed by software executing on a processor associated with the delivery system. In particular, the method starts (block 900) and proceeds to: individually sensing airflow of the breathing orifice of the patient (block 902); determining whether the breathing orifices are open to flow, the determining based on the individually sensing (block 904); and delivering the therapeutic gas by dividing the prescription titration volume among the breathing orifices open to flow (block 906). Thereafter, the method ends (block 908), likely to be restarted on the next inhalation.

Figure 10:
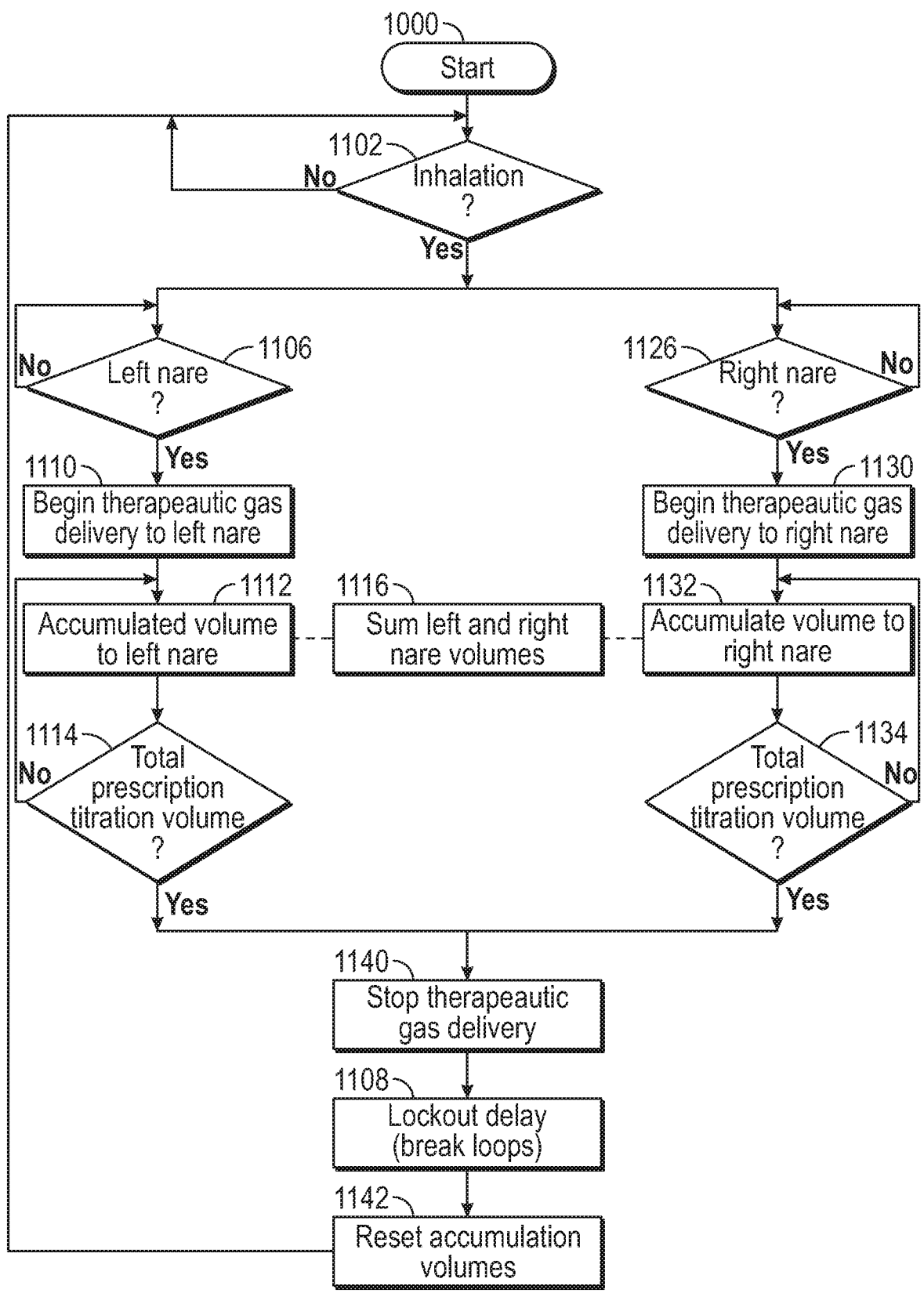
FIG. 10 shows a method in accordance with at least some embodiments.

FIG. 10 shows a method in accordance with at least some embodiments, some of which may be performed by software executing on a processor associated with the delivery system. In particular, the method starts (block 1000) and proceeds to a determination as to whether an inhalation of the patient has begun (block 1102). If no inhalation has begun, the example method loops until inhalation is detected (again block 1102). Once an inhalation has been detected, the example method takes two parallel paths, one path addressing the left nare, and one path addressing the right nare. The description starts along the path associated with the left nare. In particular, the example method determines whether there is airflow associated with the left nare (block 1106). If no airflow is sensed, the example method loops waiting for airflow (again block 1106). The loop waiting for airflow may be broken by the lockout delay (1108), discussed more below. Assuming airflow is sensed for the left nare (again block 1106), the example method begins therapeutic gas delivery to the left nare (block 1110). As soon as delivery is begun, the method also begins to accumulate an indication of volume supplied to the left nare (block 1112). For example, in systems where the volume is controlled based on delivery time, the indication of volume supplied to the left nare may be the delivery time, or an actual volume indication calculated based on delivery time. The example method then makes a determination as to whether the prescription titration volume has been provided to the patient (block 1114). The determination at block 1114 is based on all the breathing orifices to which therapeutic gas has been supplied (not just the left nare), and thus the determination may involve reference to a stand-alone summing method (block 1116) which sums the accumulated volumes across all the breathing orifices as indicated by the dashed lines associated with the method. If the full prescription titration volume has yet to be provided to patient (again block 1114), the method along the path loops until the full prescription titration volume is supplied (again block 1114).

Returning to the portion where the method proceeds down the parallel paths, again, once inhalation has been detected the example method also proceeds along the path associated with the right nare. In particular, the example method determines whether there is airflow associated with the right nare (block 1126). If no airflow is sensed, the example method loops waiting for airflow (again block 1126). The loop waiting for airflow may be broken by the lockout delay (1108), discussed more below. Assuming airflow is sensed for the right nare (again block 1126), the example method begins therapeutic gas delivery to the right nare (block 1130). As soon as delivery is begun, the method also begins to accumulate an indication of volume supplied to the right nare (block 1132). For example, in systems where the volume is controlled based on delivery time, the indication of volume supplied to the right nare may be the delivery time, or an actual volume indication calculated based on delivery time. The example method then makes a determination as to whether the prescription titration volume has been provided to the patient (block 1134). The determination at block 1134 is based on all the breathing orifices to which therapeutic gas has been supplied (and not just the right nare), and thus the determination may involve reference to the stand-alone summing method (block 1116) which sums the accumulated volumes across all the breathing orifices as indicated by the dashed lines associated with the method. If the full prescription titration volume has yet to be provided to patient (again block 1134), the method along the path loops until the full prescription titration volume is supplied (again block 1134).

Still referring to FIG. 10, the example method as shown enables not only simultaneous delivery to the nares, but also staggered delivery-start times. Consider for example, that because of a physical abnormality (e.g., a swollen turbinate) associated with one nare that initially the inhalation is only sensed through the non-blocked nare. In the example situation, once airflow is sensed for the non-blocked nare, therapeutic gas delivery is begun. However, further consider that with increase breathing effort the blocked nare opens to flow (e.g., the swollen turbinate moves out of the way and is thereafter held open by airflow through the formerly blocked nare). Once the formerly blocked nare opens to flow (and assuming the full prescription titration volume has yet to be delivered), the example method begins delivery of therapeutic gas to the formerly blocked nare (at a finite time after beginning delivery to the other nare).

Regardless of the timing as between when therapeutic gas delivery begins to each nare, once the full prescription titration flow has been delivered, the example method stops delivery of therapeutic gas for all breathing orifices (block 1140). From there, the system implements a lockout delay (block 1108), and also breaks any pending loops waiting for airflow. As for the lockout delay, delivery of therapeutic gas during the inhalation takes places at the beginning of the inhalation, and the full prescription titration volume may be delivered in a time span shorter than the time span of the inhalation itself. For example, it may take only 100 milliseconds to deliver a bolus of therapeutic gas that meets the full prescription titration volume, yet the inhalation may last a second or more. In order to reduce the chances of double delivery of therapeutic gas in the same inhalation, the lockout delay (block 1108) implements a time delay to ensure the current inhalation has ceased before the method begins inhalation detection anew (at block 1102). As for the "break loops" aspect, as noted above the example method proceeds along parallel paths. If one nare is blocked to flow (and thus one path may be in a loop waiting for inhalation of that nare to begin), once the full prescription titration volume has been provided the software loop is broken, thus enabling the method to begin sensing anew (at block 1102) for the next inhalation.

Finally, once the lockout delay (block 1108 has ended), the example method resets the accumulated volumes (block 1142), and begins anew (at block 1102) sensing the next inhalation.

The example method of FIG. 10 references only the nares of a patient; however, one of ordinary skill, with the benefit of this disclosure and now understanding the implementation with respect to the nares, could adapt the method of FIG. 10 to include a parallel path for oral delivery. Moreover, one of ordinary skill, with the benefit of this disclosure and now understanding the implementation with respect to the nares, could adapt the method of FIG. 10 to treat the nares as a single unit with respect to one of the parallel paths, and treat the mouth along the second parallel path.

The above discussion is meant to be illustrative of the principles and various embodiments of the present invention. Numerous variations and modifications will become apparent to those skilled in the art once the above disclosure is fully appreciated. It is intended that the following claims be interpreted to embrace all such variations and modifications.

What is claimed is:

1. A conserver system comprising:
 a therapeutic gas port configured to couple to a source of therapeutic gas;
 a first port configured to fluidly couple to a first breathing orifice of a patient;
 a first sensor associated with the first port, and a first valve fluidly coupled between the therapeutic gas port and the first port;
 a second port configured to fluidly couple to a second breathing orifice of the patient;
 a second sensor associated with the second port, and a second valve fluidly coupled between the therapeutic as port and the second port;
 a processor electrically coupled to the first sensor and the first valve, and the processor electrically coupled to the second sensor and the second valve;
 a memory coupled to the processor, the memory storing a program that, when executed by the processor, causes the processor to:
  fluidly couple, during a first inhalation, the therapeutic gas port to the first port by way of the first valve when airflow through the first breathing orifice is sensed by the first sensor;
  refrain, during an initial portion of the first inhalation, from fluidly coupling the therapeutic gas port to the second port when airflow through the second breathing orifice is not sensed by the second sensor; and then
  fluidly couple, during a subsequent portion of the first inhalation of the patient, the therapeutic gas port to the second port by way of the second valve when airflow through the second breathing orifice is later sensed by the second sensor; and
  decouple the therapeutic gas port from the first and second ports when a volume of therapeutic gas delivered to the first and second breathing orifices equals a prescription titration volume.

2. The conserver system of claim 1, wherein the first sensor is a first pressure sensor fluidly coupled to the first port, the first pressure sensor configured to sense airflow of the first breathing orifice based on changes in sensed pressure.

3. The conserver system of claim 2, wherein the second sensor comprises at least one selected from the group consisting of a pressure sensor and a flow sensor.

4. The conserver system of claim 1, wherein the first sensor comprises a first flow sensor fluidly coupled within a flow path of the first port, the first flow sensor configured to sense airflow of the first breathing orifice drawn through the first port.

5. The conserver system of claim 4, wherein the second sensor comprises at least one selected from the group consisting of a pressure sensor and a flow sensor.

6. The conserver system of claim 1, wherein the program further causes the processor to:
- accumulate, during the first inhalation, a first indication of volume applied to the first breathing orifice;
- accumulate, during the first inhalation, a second indication of volume applied to the second breathing orifice; and
- sum the first and second indications of volume to create a first sum value;
- wherein when the processor decouples the therapeutic gas port from the first and second ports, the program further causes the processor to decouple when the first sum value meets a value indicative of the prescription titration volume.

7. The conserver system of claim 1, wherein the program further causes the processor to:
- fluidly couple, during a second inhalation of the patient, the therapeutic gas port to the second port by way of the second valve when airflow through the second breathing orifice is sensed by the second sensor;
- refrain, during an initial portion of the second inhalation of the patient, from fluidly coupling the therapeutic gas port to the first port when airflow through the first sensor is not sensed; and then
- fluidly couple, during a subsequent portion of the second inhalation of the patient, the therapeutic gas port to the first port by way of the first valve when airflow through the first breathing orifice is later sensed by the first sensor; and
- decouple the therapeutic gas port from the first and second ports when a volume of therapeutic gas delivered to the first and second breathing orifices during the second inhalation equals the prescription titration volume.

8. The conserver system of claim 7, wherein the program further causes the processor to:
- accumulate, during the second inhalation, a third indication of volume applied to the first breathing orifice;
- accumulate, during the second inhalation, a fourth indication of volume applied to the second breathing orifice; and
- sum the third and fourth indications of volume to create a second sum value;
- wherein when the processor decouples the therapeutic gas port from the first and second ports associated with the second inhalation, the program further causes the processor to decouple when the second sum value meets the value indicative of the prescription titration volume.

9. A conserver system comprising:
- a therapeutic gas port disposed on an outside surface of the conserver system;
- a first port disposed on an outside surface of the conserver system, a first sensor associated with the first port, and a first valve fluidly coupled between the therapeutic gas port and the first port;
- a second port disposed on an outside surface of the conserver system, a second sensor associated with the second port, and a second valve fluidly coupled between the therapeutic gas port and the second port;
- a processor electrically coupled to the first sensor, the first valve, the second sensor, and the second valve;
- a memory coupled to the processor, the memory storing a program that, when executed by the processor, causes the processor to, during a first inhalation:
  - fluidly couple the therapeutic gas port to the first port by way of the first valve when airflow through the first port is sensed by the first sensor;
  - refrain from fluidly coupling the therapeutic gas port to the second port when airflow through the second port is not sensed by the second sensor during an initial portion of the first inhalation; and then
  - fluidly couple the therapeutic gas port to the second port by way of the second valve when airflow through the second breathing orifice is later sensed by the second sensor during a subsequent portion of the first inhalation; and
  - decouple the therapeutic gas port from the first and second ports when a volume of therapeutic gas delivered to the first and second ports equals a prescription titration volume.

10. The conserver system of claim 9:
- wherein the program further causes the processor to, during the first inhalation:
  - accumulate a first indication of volume applied to the first breathing orifice;
  - accumulate a second indication of volume applied to the second breathing orifice; and
  - sum the first and second indications of volume to create a first sum value;
  - wherein when the processor decouples the therapeutic gas port from the first and second ports, the program further causes the processor to, during the first inhalation, decouple when the first sum value meets a value indicative of the prescription titration volume.

11. The conserver system of claim 9, wherein the program further causes the processor to, during a second inhalation distinct from the first inhalation:
- fluidly couple the therapeutic gas port to the second port by way of the second valve when airflow through the second port is sensed by the second sensor;
- refrain from fluidly coupling the therapeutic gas port to the first port when airflow through the first sensor is not sensed by the first sensor during an initial portion of the second inhalation; and then
- fluidly couple the therapeutic gas port to the first port by way of the first valve when airflow through the first port is later sensed by the first sensor during a subsequent portion of the second inhalation; and
- decouple the therapeutic gas port from the first and second ports when a volume of therapeutic gas delivered to the first and second breathing orifices during the second inhalation equals the prescription titration volume.

12. The conserver system of claim 11:
- wherein the program further causes the processor to, during the second inhalation:
  - accumulate a third indication of volume applied to the first breathing orifice;
  - accumulate a fourth indication of volume applied to the second breathing orifice; and
  - sum the third and fourth indications of volume to create a second sum value;
- wherein when the processor decouples the therapeutic gas port from the first and second ports associated with the second inhalation, the program further causes the processor to, during the second inhalation, decouple when the second sum value meets the value indicative of the prescription titration volume.

* * * * *